(12) United States Patent
Sidebotham

(10) Patent No.: US 7,909,883 B2
(45) Date of Patent: Mar. 22, 2011

(54) PERCUTANEOUS IMPLANT FOR LIMB SALVAGE

(76) Inventor: Christopher G. Sidebotham, Mendham, NJ (US)

( * ) Notice: Subject to any disclaimer, the term of this patent is extended or adjusted under 35 U.S.C. 154(b) by 792 days.

(21) Appl. No.: 11/709,397

(22) Filed: Feb. 21, 2007

(65) Prior Publication Data

US 2008/0200995 A1   Aug. 21, 2008

(51) Int. Cl.
  *A61F 2/28*  (2006.01)
  *A61F 2/78*  (2006.01)
  *A61F 2/74*  (2006.01)
  *A61F 2/02*  (2006.01)

(52) U.S. Cl. ...... 623/23.55; 623/32; 623/27; 623/11.11; 623/23.5; 623/23.53; 623/16.11

(58) Field of Classification Search ............ 623/32, 623/23.46, 23.55, 27, 11.11, 23.53, 16.1
See application file for complete search history.

(56) References Cited

U.S. PATENT DOCUMENTS

| | | | |
|---|---|---|---|
| 3,947,897 A | 4/1976 | Owens | 3/2 |
| 4,143,426 A | 3/1979 | Hall et al. | 3/6 |
| 4,158,895 A | 6/1979 | Reswick et al. | 3/2 |
| 4,881,536 A | 11/1989 | Noble et al. | 606/94 |
| 4,919,670 A * | 4/1990 | Dale et al. | 623/19.14 |
| 5,041,137 A | 8/1991 | Nemoshkalov | 623/16 |
| 5,169,597 A | 12/1992 | Davidson et al. | 428/613 |
| 5,181,928 A | 1/1993 | Bolesky et al. | 623/23 |
| 5,571,193 A | 11/1996 | Kampner | 623/18 |
| 5,593,410 A * | 1/1997 | Vrespa | 606/312 |
| 5,986,169 A | 11/1999 | Gjunter | 424/422 |
| 6,197,065 B1 | 3/2001 | Martin et al. | 623/23.17 |
| 6,264,699 B1 * | 7/2001 | Noiles et al. | 623/23.23 |
| 6,425,925 B1 * | 7/2002 | Grundei | 623/32 |
| 6,464,728 B1 | 10/2002 | Murray | 623/22.42 |
| 6,482,238 B1 | 11/2002 | Grundei | 623/32 |
| 6,485,522 B1 | 11/2002 | Grundei | 623/38 |
| 6,494,918 B1 | 12/2002 | Pope et al. | 623/23.6 |
| 6,843,808 B2 | 1/2005 | Grundei | 623/32 |
| 6,869,450 B2 * | 3/2005 | Grundei | 623/32 |
| 6,981,991 B2 * | 1/2006 | Ferree | 623/23.46 |

(Continued)

FOREIGN PATENT DOCUMENTS

DE   19931882 C1   3/2001

(Continued)

*Primary Examiner* — David Isabella
*Assistant Examiner* — Jacqueline Woznicki
(74) *Attorney, Agent, or Firm* — Ernest D. Buff & Associates; Ernest D. Buff; Margaret A. LaCroix

(57) ABSTRACT

A percutaneous implant device is biologically attached to bone and soft tissue of a broken limb or amputated limb without longitudinal or lateral movement. Bone and soft tissue in-growth are promoted. The percutaneous implant device has a bio-compatible metal alloy stem member, having an integral tapered fluted section designed to fit into a taper reamed bone canal. A precisely dimensioned cylindrical central core cooperates with a suture ring and an external extension member, facilitating attachment of the percutaneous implant device to a hand or foot prosthesis. A porous metal outer body having a female taper at one end and the capacity to promote growth of bone and soft tissue, is press fitted on the central core contacting suture ring. The assembled implant is inserted into a taper reamed bone cavity until the male taper-reamed bone free end contacts the female taper. Soft skin is extended over the outer surface of the porous metal outer body and the surrounding suture ring.

10 Claims, 12 Drawing Sheets

U.S. PATENT DOCUMENTS

| | | | |
|---|---|---|---|
| 7,014,661 B2 * | 3/2006 | Blunn et al. | 623/23.57 |
| 7,018,420 B2 * | 3/2006 | Grundei | 623/32 |
| 7,141,073 B2 * | 11/2006 | May et al. | 623/32 |
| 7,223,293 B2 | 5/2007 | Kristensen | 623/32 |
| 7,374,577 B2 * | 5/2008 | Kim et al. | 623/32 |
| 2004/0172138 A1 * | 9/2004 | May et al. | 623/20.36 |
| 2004/0230312 A1 * | 11/2004 | Hanson et al. | 623/21.12 |
| 2005/0071014 A1 | 3/2005 | Barnett et al. | 623/19.14 |
| 2005/0216090 A1 * | 9/2005 | O'Driscoll et al. | 623/20.32 |
| 2006/0020346 A1 * | 1/2006 | Hunter et al. | 623/23.51 |
| 2006/0041318 A1 * | 2/2006 | Shannon | 623/23.46 |
| 2006/0178752 A1 | 8/2006 | Yaccarino et al. | 623/23.63 |
| 2006/0235402 A1 | 10/2006 | Celli et al. | 606/293 |
| 2006/0241776 A1 | 10/2006 | Brown et al. | 623/20.16 |
| 2007/0073412 A1 * | 3/2007 | Blunn et al. | 623/23.44 |
| 2008/0058957 A1 * | 3/2008 | Newcombe et al. | 623/32 |
| 2009/0062928 A1 * | 3/2009 | Pitkin | 623/32 |

FOREIGN PATENT DOCUMENTS

| | | |
|---|---|---|
| EP | 1559383 | 3/2005 |
| JP | 01085645 A * | 3/1989 |
| WO | WO 99/65426 | 6/1998 |

* cited by examiner

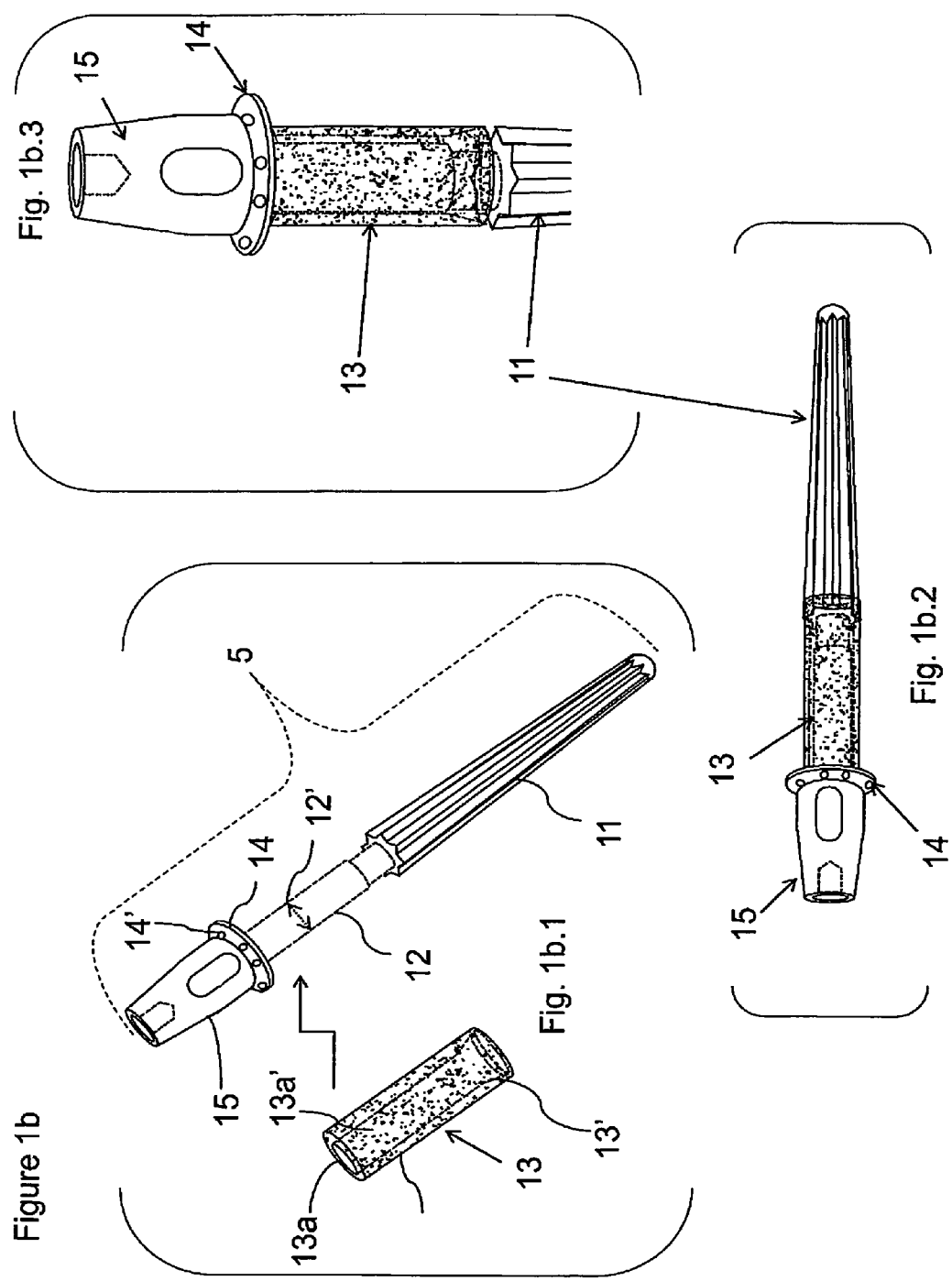

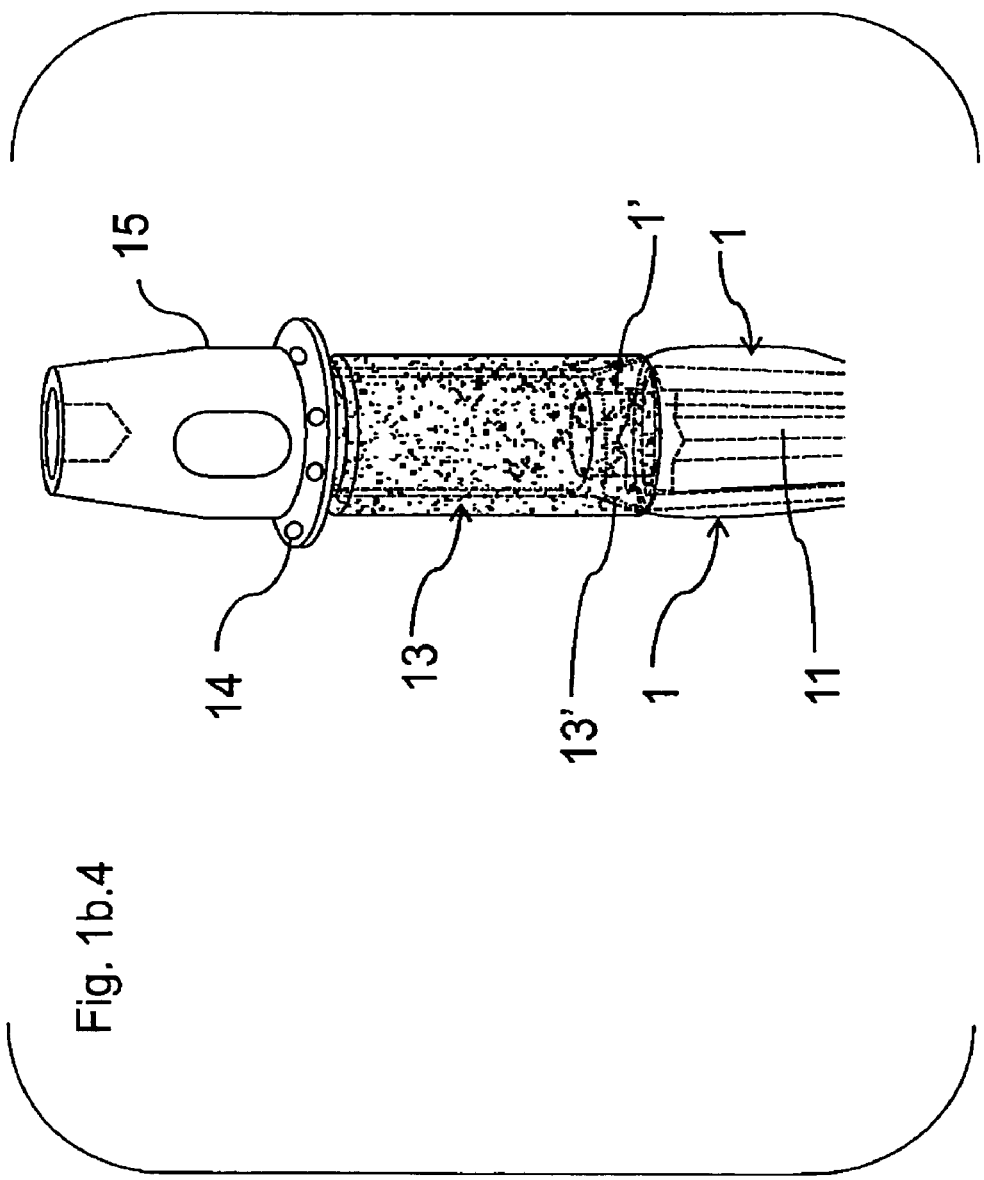
Fig. 1b.4

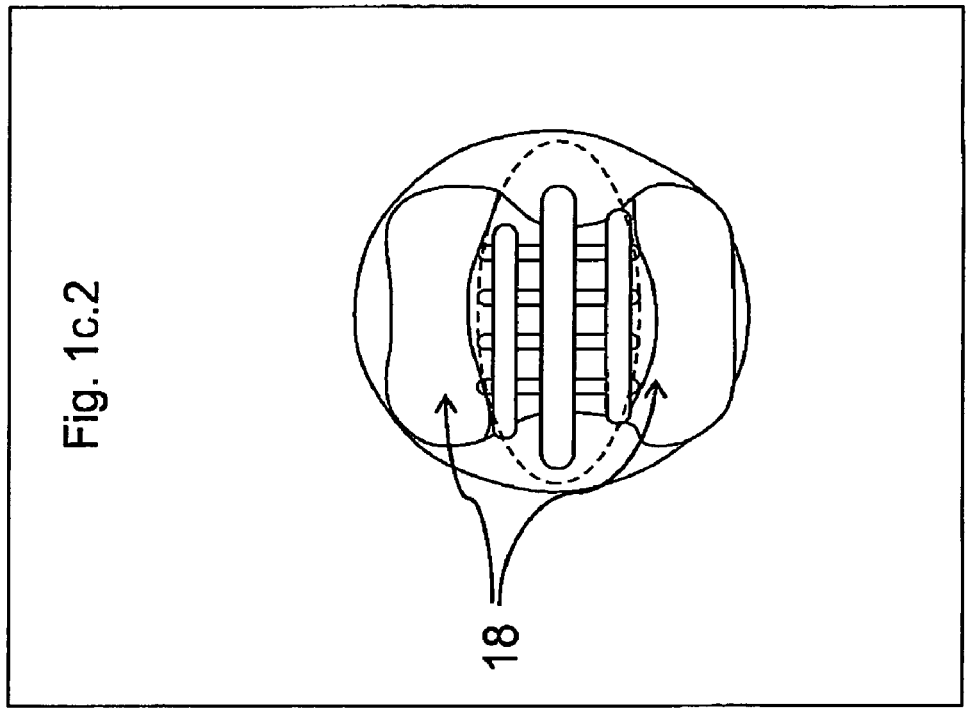
Fig. 1c.1
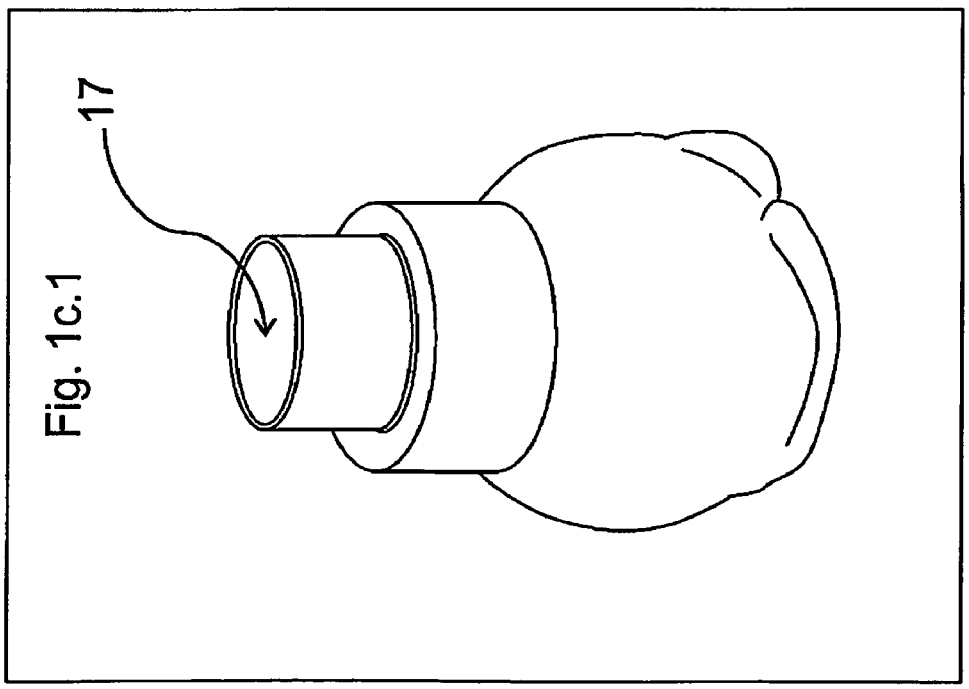
Fig. 1c.2

PERCUTANEOUS IMPLANT FOR LIMB SALVAGE

BACKGROUND OF THE INVENTION

1. Field of the Invention

The present invention relates to implant devices for replacement of amputee limbs; and more particularly to replacement of amputee limbs with a percutaneous implant device that physiologically loads both bone and soft tissue.

2. Description of the Prior Art

Many patents address issues related to implant devices that attach to amputee limbs. These devices typically carry features that facilitate attachment of prosthesis to the implanted device. Some of the implanted devices have a hinge present within the implanted device to function as a knee or elbow joint. One of the devices has an extension that attaches to the Achilles tendon, to provide a connection having a skin attachment. The attachment of the bone to the implant is accomplished through use of a methacrylate or appetite adhesive, or by using a thin layer of porous body, such as netting. There is no disclosure or suggestion concerning a device capable of biologically bonding the implant to the bone while, at the same time, creating biological attachment of soft tissue and skin, which thereby provides a continuously bonded structure that resembles a natural bone with entirely bonded skin and soft tissue.

U.S. Pat. No. 3,947,897 to Owens discloses an apparatus for connecting a prosthesis to a bone. This apparatus is used to connect a prosthesis to a bone of a stump of an amputated limb such as the arm or leg of a person. The apparatus includes a tubular female socket adapted to be inserted within an intermedullary cavity of the bone. The tubular socket has an open lower end with a sleeve of bio-compatible material permitting access through the skin of the amputee's stump. A stainless steel, tubular socket having a roughened outer surface is fitted into a bone canal, and the exposed end of the sleeve is covered with a biocompatible material, over which the skin is extended to heal the skin attachment. There is no bond between the free end of the inserted socket and the sleeve of biocompatible material. Stainless steel does not allow in-growth of bone. Even though the skin may be attached to the porous sleeve, the lack of connection between the socket and the sleeve prevents the skin from being attached in the same manner as the bone. The latter has practically no bone in-growth, just forced fit. The tubular sleeve has attachment hardware for securing an externally inserted prosthesis.

U.S. Pat. No. 4,143,426 to Hall et al. discloses a permanently attached artificial limb. This permanently attached artificial limb comprises an endoprosthesis in combination with an artificial tendon attachment. The artificial tendon attachment permits the use of existing skeletal muscles to power external articulating mechanical joints of the endoprosthesis device. The artificial tendon penetrates the skin and provides a strong interface with existing skeletal muscles. This implant has a porous polymethyl methacrylate bond between the bone and the intramedullary rod and this cemented bonding procedure does not result in bone in-growth. The open end of the intramedullary rod is covered with velour fabric, e.g. of nylon or Dacron, to allow skin attachment at the skin interface. There is no direct bond between this velour fabric and the intramedullary rod. Therefore, this device does not attach the bone tissue to the intramedullary rod by bone in-growth. It also does not attach any portion of the implant that connects the intramedullary rod to soft tissue by tissue in-growth. An artificial tendon is attached to a velour covered silicone (Silastic) ball, which in turn is connected to a velour sheath, which is attached to the stub of the Achilles tendon to allow muscle directed movement of the prosthesis.

U.S. Pat. No. 4,158,895 to Reswick et al. discloses a prosthesis coupling. A stainless steel socket is inserted into a bone cavity and bonded with methylmethacrylate creating a cemented bond that does not result in bone in-growth. One end of a silicone flexible coupling is attached to the socket, and the other end of the silicone coupling is connected to a vitreous carbon sleeve. The skin is stitched over the vitreous carbon, allowing skin attachment. The skin seal thus created at the sleeve is not broken when the user moves an implant inserted into the sleeve due to the flexibility of the silicone coupling which essentially floats the skin seal. The skin or soft tissue attachment does not work in coherence with the movement of the bone, owing to the flexibility of the coupling. The attachment of the bone to the implant is only accomplished through a cement bond. Accordingly, there is no bone in-growth.

U.S. Pat. No. 4,881,536 to Noble et al. discloses a method and apparatus for prosthesis placement. This surgical procedure is for orthopedic implantation of prosthesis. Cobalt chromium or stainless steel prosthesis is placed in a bone cavity that is filled with a viscous polymer that hardens to permanently attaché the prosthesis to the bone cavity. There is no bone in-growth between the prosthesis and the bone. There is no attachment of the soft tissue to the prosthesis.

U.S. Pat. No. 5,041,137 to Nemoshkalov discloses a method for prosthetic restoration of human limbs. This device for prosthetic restoration of human limbs comprises a supporting member for the stump, shaped as a spherical bowl and connected to the prosthesis of the limb missing portion, and a fixing contrivance interconnecting the stump bone and the supporting member. The supporting member is made of a material indifferent to living tissue and its diameter corresponds to the stump outside diameter. This device has a tapered rod that is inserted into a bone cavity that is bonded using an acrylic resin binder that hardens in 5-7 minutes. There is no bone in-growth joint between the inserted rod and bone tissue. A support body with a porous surface coating is attached to the inserted rod by a threaded screw. The top outer surface of the supporting member, which is made of a porous material, only serves as a support for the stump bone, which contacts the bone in a very limited area. Bone in-growth in this limited region is negligible, causing the implanted taped rod to be predominantly held in place by the acrylic resin. The top surface of the porous supporting member contacts the soft tissue and muscles providing soft tissue in-growth. The skin is merely wrapped around the porous support member, which provides soft tissue in-growth attachment. This device does not provide simultaneous in-growth of both bone and soft tissue.

U.S. Pat. No. 5,169,597 to Davidson et al. discloses a biocompatible low modulus titanium alloy for medical implants. This biocompatible titanium alloy has low elastic modulus and contains titanium, with about 10-20 wt. % or 35-50 wt. % niobium and up to 20 wt. % zirconium useful for fabricating of orthopedic implants. More typically, the alloy is 74% Ti with 13% of each of Zr and Nb. The modulus of elasticity of the alloy is typically 84 GPa, similar to a bone modulus of elasticity. The alloy has high strength, typically greater that 979 MPa. Portions of the implant may be coated with porous bead or wire mesh coating.

U.S. Pat. No. 5,181,928 to Bolesky et al. discloses a modular hip prosthesis. This modular hip prosthesis is provided for the replacement of a portion of the femur. The prosthesis is assembled from a kit that includes a stem member having an upper portion and a lower portion, with the lower portion sized to be received in the femur. The kit also includes a body member that is sized to replace a portion of the femur and is configured to be received over the upper portion of a stem member. The kit also includes a head member that is sized to replace the head of the femur. A neck member is provided to attach the head member to the body member to form an assembled prosthesis. The modular hip prosthesis has a central stem that is bonded to the bone by a grouting material or bone cement material. There is no bone in-growth attachment of the central stem and the bone. The soft tissue is not attached to the implanted stem. Soft tissue is not attached to the body member that is attached to the upper portion of the stem to attach to a prosthesis.

U.S. Pat. No. 5,571,193 to Kampner discloses an implant with a reinforced resorbable stem. This prosthetic implant for a bone joint has an anchor formed of a resorbable sleeve reinforced with a nonresorbable core. The implant has a central non-absorbable metallic core surrounded by an anchor made from a resorbable material. The anchor creates an interference fit between the implant and the bone cavity and slowly disintegrates as the bone ingrowth occurs. At this point, the central metallic core becomes detached and no longer carries any load, allowing the bone ingrowth to carry all the loading. This method creates a dangerous situation when the implant is first incorporated, since the metallic core is not in any manner attached to the anchor. Moreover, the ingrowth of the bone into the anchor progressively destroys the integrity of the resorbable layer, while the bone structure is yet to be built completely for load sharing. The presence of a non-load carrying metallic core reduces the overall cross section of the bone, reducing its load capacity. There is no bone in-growth attachment connecting the bone to the metallic core. All of the load must be accommodated by the resorbable material with some bone in-growth.

U.S. Pat. No. 6,197,065 to Martin et al. discloses a method and apparatus for segmental bone replacement. This bone attachment assembly is for reattaching of a remaining portion of a long bone diaphysis following resection. The assembly includes a main body, an anchor for anchoring the device with respect to the remaining bone portion and an attachment portion for attaching the main body to the anchor. The assembly may be connected to an orthopedic appliance, an interposed orthopedic appliance connected to a second bone attachment assembly, or a transcutaneous bar for attaching an external appliance. The first portion of the broken bone is milled to a preselected convex conical geometry. The main body of the implant is milled with a concave conical geometry and coated with bone in-growth material. The central portion of the implant has a tapered section. It is inserted into the bone canal. A cylindrical section thereof fits against the bone and is said to prevent lateral movement. There is no bone in-growth in this cylindrical region of the implant. The implant has a central aperture that has a threaded compliant connecting rod that is screwed into the implant on one side. The distal side of the connecting rod is placed within the bone cavity and is anchored by a plurality of transverse anchor bodies. Due to this compliancy of the connecting rod, the implant is only held by the fit at the cylindrical region. It awaits bone in-growth at the conical portion, which takes substantial time. The compliant rod provides no support since it is said to be compliant. There is no provision in this device for soft tissue in-growth.

U.S. Pat. No. 6,425,925 to Grundei discloses a leg exoprosthesis for adaptation to a thigh stump. This leg exoprosthesis is appointed for adaptation to a thigh stump, and has an adapter for a knee joint. The knee joint is mounted and coupled to a lower leg prosthesis. A bridle band force-transmitting element is coupled to the lower leg prosthesis for introducing extending forces. This device is a replacement for a knee joint having one end attached to the broken bone. The connection to bone does not have bone in-growth provisions. The stump portion is merely sealed with no provision for soft tissue in-growth.

U.S. Pat. No. 6,464,728 to Murray discloses a modular neck for femur replacement surgery. This prosthesis is provided for femur replacement surgery. It has a stem, which is received in the femur. A modular neck is removably attached to the stem so that its angle of protrusion can be customized by the surgeon. The stem passes through a sleeve inserted into the bone canal, which has a press fit with respect the bone cavity. Thus, the implanted stem does not directly contact the bone cavity. A sliding movement of the sleeve allows for micro-motion, redistributing stress at the implanted location. The stem does not have a bone in-growth coating, and these micro-motions will result in poor bone in-growth. Also there is no provision for soft tissue in-growth attachment.

U.S. Pat. No. 6,482,238 to Grundei discloses an upper leg stump endoprosthesis for an exoprosthetic provision. This upper leg stump endoprosthesis is designed for an exoprosthetic provision of a patient having undergone above-knee amputation. The upper leg stump can be inserted into a shank to which a below-knee prosthesis with a foot part is fitted. The prosthesis includes a proximal shaft, which is implantable in a truncated femur. An open-mesh, three-dimensional netting structure covers at least partially the proximal shaft. An adapter is connected to a distal end of the proximal shaft. A substitute condyle element, constituting a replica of a natural condyle of a knee joint, is linked to said shaft by the adapter. The resulting device comprises a knee joint that is attached to the stump bone. The attachment includes a mesh that surrounds the insertion stem and is said to promote bone ingrowth. There is no attachment of soft tissue by in-growth. Moreover, the attachment of the bone tissue with the stem is questionable, since there is no physical bond between the net and the stem.

U.S. Pat. No. 6,485,522 and Foreign Patent Application No. WO 9965426 to Grundei disclose an adapter for an exoprosthetic standard element. This adapter is for an exoprosthetic standard element such as an exoprosthetic knee joint. The adapter can be inserted with a proximal handle part into a tubular bone stump. The proximal handle part is at least partly covered with a three-dimensional open-loop network structure, and at its distal end has a coupling device for the standard element. The device has a stem that is inserted into a bone canal. The stem has a coating of an open-mesh, three-dimensional space-network structure, through which bone materials can grow. There is no attachment of soft tissue permitting soft tissue in-growth.

U.S. Pat. No. 6,494,918 to Pope et al. discloses a component for a prosthetic joint having a diamond load bearing and articulation surface. The prosthetic joint comprises a substrate that includes a solvent-catalyst metal, a diamond layer sintered to said substrate. A zone between the substrate and the diamond layer has a composition gradient of decreasing solvent-catalyst metal content across the zone. The chemical bonds in the zone include chemical bonds including diamond-to-diamond bonds in the diamond table, diamond-to-metal bonds in the gradient transition zone, and metal-to-metal bonds in the solvent-catalyst metal. A mechanical grip between said diamond layer and the substrate tends to secure the diamond layer to the substrate. The load bearing surfaces where movement occurs such as a ball joint have a polycrystalline diamond coating to reduce friction and wear. The disclosure of the '918 patent does not suggest inserting and attaching an implant.

U.S. Pat. No. 6,843,808 to Grundei discloses subcutaneous, intramuscular coupling for a rigid transcutaneous implant. This subcutaneous, intramuscular bearing is for a rigid transcutaneous implant that can be anchored intracorporeally in a bone stump. The implant has an extracorporeal coupling device for a standard exoprosthetic component that includes a flexible material, and that has a socket that distally surrounds the implant in a firm manner. The bearing includes an enveloping sheath arranged intracorporeally in the form of a flexible pleated bellows. The sheath is proximally connected to the socket via a collar that is formed in a sealing manner. Formation of the collar is such that a hollow space with a minimum breadth s remains free between the inner walling of the pleated bellows and the outer walling of the socket. A flexible grid network is arranged distally at the pleated bellows. An additional grid network adjoins the flexible grid network on the distal side, wherein the additional grid network has a higher modulus of elasticity in comparison to that of the flexible grid network. The stem component is inserted into a cavity in the bone and has an enveloping adapter. A tube or socket is glued to the implant stem. An enveloping sheath in the form of bellows is attached to a collar on the tube or socket providing flexibility. The bottom portion of the bellows is attached to an open cell grid with apertures for attaching the skin. The skin attachment is not load transferring with the bone attachment due to the presence of pleated bellows, which inherently generates relative movement between the bone and the skin. Moreover, there is no porous or open mesh material in direct contact with the bone of the femur. There is also no direct attachment of the open mesh grid and the implant stem.

U.S. Pat. No. 6,869,450 and Foreign Patent Application No. DE 19931882 C1 to Grundei disclose a subcutaneous, intramuscular support for a rigid transcutaneous implant. This subcutaneous, intramuscular support is provided for a rigid transcutaneous implant, which can be anchored intracorporeally in a bone stump. The support has an intermediate piece between the part of the implant to be intracorporeally anchored and an extracorporeal coupling device that can be coupled to it. A rigid bushing is firmly connected with the intermediate piece, such that an annulus is formed between the wall of the bushing and the intermediate piece, the annulus being closed in the intracorporeal direction, and into which annulus the extracorporeal coupling device can be inserted. A tube made of a flexible material is applied to the outer wall of the bushing, and a metallic wool is applied to the flexible tube. The stem component is inserted into a cavity in the bone and has a metal sleeve with a conical clamping sleeve. An intermediate piece is force fitted into the implant stem. A flexible bushing with silicone collar and metallic mesh flexible collar is attached to the intermediate piece. The bottom portion of the flexible bushing is attached to a open cell grid with apertures for attaching the skin. The skin attachment is not load transferring with the bone attachment due to the presence of pleated bellows, which inherently generates relative movement between the bone and the skin. Moreover, there is no porous or open mesh material in direct contact with the bone of the femur. There is also no direct attachment of the open mesh grid and the implant stem.

U.S. Pat. No. 7,014,661 to Blunn et al. discloses a transcutaneous prosthesis. The transcutaneous prosthesis comprises a first component shaped for implantation into a bone, a second component intended for location between the bone and the skin, and a third component intended for location exterior to the skin surface, having a low surface energy, which deters bacterial adhesion. The prosthesis has three discrete components. The first component has longitudinally extending flutes that engage with the bone. The surface of the first component may be coated with apatite or micropitted, There is no indication that the material used is a biocompatible titanium or cobalt chromium alloy. The second component is cylindrical and extends from the first component. It is also coated with a surface treatment to attach to the bone. This surface treatment is not indicated to be a porous coating of any nature. The attachment to soft tissue is to be carried immediately during surgery or wait until the bone healing is complete. The attachment to skin is by using alumina oxide or apatite. However, there is no attachment between any of these coating materials and the stem, in particular, the skin which contacts loose aluminum oxide or apatite.

U.S. Pat. No. 7,018,420 to Grundei discloses a subcutaneous, intramuscular bearing for a rigid transcutaneous implant. The subcutaneous, intramuscular bearing for a rigid transcutaneous implant is provided, for anchoring intracorporally in a bone stump. The bearing has an intermediate piece between the implant and an extracorporal coupling for coupling on the implant. A rigid bushing is tightly connected to the intermediate piece, such that between the wall of the bushing and the intermediate piece an annular space is formed, which is closed in the intracorporal direction, for receiving and setting the extracorporal coupling. The outer wall of the bushing has an open-meshed, three-dimensional lattice structure and a lattice-free distal region having a width 'B'. A spring ring is set in the annular space from the distal end, moved with a telescoping motion, and locked under exertion of its spring effect. This device has a stem with a flared end. The whole surface of the stem has a three-dimensional, open-meshed lattice structure designed for bone in-growth and tissue in-growth. After this initial attachment, a second piece is inserted which also has the three-dimensional, open-meshed lattice structure and is expected to attach to soft tissue. Since all the soft tissue is already used in the first stage of the operation, this second soft tissue attachment is not likely. Besides, the presence of a spring allows movement between two skin in-growth regions, creating skin stress.

Foreign Patent Application No. EP 1559383 to Grundei discloses a set for constructing a transcutaneous implant. A femur implant has an adapter for an exoprothetic standard component with a proximal shank. The shank has a three-dimensional open mesh structure. The shank distal end has a link-interface for the standard exoprothetic standard component. From the figure it appears that the stem is provided with open celled lattice for attachment within the one canal. Presence of the open celled lattice in the bottom portion indicates that there is bone attachment in more than one place. There appears to be a hinge provided within the stem. And a prosthesis may be attached at the distal end. There appears to be no soft tissue attachment. If any soft tissue attachment occurs in the distal bottom end, as indicated by the open celled lattice, the skin will be highly stretched.

There remains a need in the art for a percutaneous implant for humans and animals (i) that is capable of being attached to a broken or amputated bone; (ii) that successfully attaches the implant to both bone and soft tissue; (iii) that provides a natural extension of the amputated limb; and (iv) that comprises a skin attachment which prevents entry of infectious microorganisms. The percutaneous implant carries one of several prosthesis.

SUMMARY OF THE INVENTION

The percutaneous implant device comprises a tapered fluted bone compatible metal alloy stem appointed to be inserted within a surgically created bone canal. The stem has an inner cylindrical core integrally attached to the tapered fluted stem with an outer diameter having precise dimensional tolerance to receive a press fitted porous outer body member that has a central aperture matching the outer diameter dimension of the cylindrical core. The porous outer body member is preferably made from sintered tantalum beads or wire, or metal foam, and is inserted from the tapered fluted end of the stem and rests against a suture ring member integrally formed on the stem. The side of the porous outer member distal from the suture ring has a female taper provided. The surgeon during the surgical procedure drills a tapered hole within the bone canal to a pre-determined length matching the dimension of the stem. The free end of the bone is machined to have a male taper matching the female taper provided in the porous outer body. Thus when the percutaneous device is implanted into the bone cavity, the taper of the stem binds against the fluted tapered stem portion, while the male taper of the bone free end precisely mates with the female tapered end of the porous outer member. The tapered attachment of the bone with that of the porous outer member that is press fitted against the stem that carries the fluted tapered end securely holds the percutaneous implant against the bone. Now the soft tissue is drawn contacting the porous outer body and allowed to enclose the suture ring wherein it is stitched in a conventional manner using holes provided in the suture ring.

Since the male tapered bone free end contacts the female tapered end of the porous outer body, the bone grows into the pores of the porous outer body forming biological attachment. This bone growth may extend as much as 0.5 to 1 inch, converting the porous outer body to a composite of bone and titanium while the press fit against the cylindrical portion of the inner core of the stem becomes tighter. Since the porous outer body also contacts the soft tissue over a significant distance, it tends to grow and enter the pores of the metal porous body, creating biological attachment of the soft tissue to the same member, and providing biological attachment to the bone. This creates a stable natural attachment of the percutaneous implant, which resembles the native attachment of a bone tissue to soft tissue. Since the skin is stitched around the suture ring, which is part of the stem, the latter, being made from the bio-compatible metal alloy, promotes biological attachment of the skin to the suture ring.

Immediately after the surgical procedure of the percutaneous implant in an amputated limb, the implant is held in place by three key elements. First, the fluted tapered stem engages with the tapered fluted bone cavity prepared by the surgeon due to the force applied to the distal end of the stem. Secondly, the male tapered end of the bone engages the female tapered end of the porous metal outer body that is press fitted against the outer diameter of the inner core portion of the stem, and at the same time rests against the suture ring. Thirdly, the soft tissue surrounds the outer surface of the porous metal outer body for a significant length and the skin is sutured, surrounding the surrounding suture ring. These attachment means secure the percutaneous implant against the bone tissue and soft tissue and prevent any lateral or longitudinal movement, allowing both bone in-growth and attachment as well as soft tissue in-growth and attachment at the same time. Due to this secure attachment, the percutaneous implant heals without substantial pain and results in high quality bone tissue in-growth and soft tissue in-growth without the formation of soft bone tissue that lacks strength, commonly observed when implants have movement in this critical healing period.

The percutaneous implant device is designed for replacement of amputee limbs. The device physiologically loads both bone and soft tissue. Preservation of bone and tissue is promoted, thereby mitigating or substantially eliminating pain associated with strapping a prosthetic to the stump. Advantageously, the implant device provides a prosthesis, which allows for biological attachment directly to the bone and soft tissues. The percutaneous implant device includes an external portion of the implant body that provides an attachment for an extremity, such as foot or hand prosthesis. In addition, the inner core is made of metal alloy that imparts strength and biocompatibility. A porous outer body member is press fitted over the inner core. The porous outer body member is preferably composed of a tantalum or titanium porous material capable of allowing bone and soft tissue to grow into it.

Generally stated, the invention involves a percutaneous implant device that broadly comprises: (i) a male tapered fluted stem appointed to be inserted within a female tapered bone canal; (ii) an inner cylindrical core that is integral with said tapered fluted stem; (iii) a porous outer body member press fitted to said inner core cylindrical portion therein; (iv) a free end of the porous outer body provided with a female taper to seat the porous outer body member against a male taper at the extremity of the bone, preventing lateral movement; (v) a suture ring member integral with the stem, the suture ring member being distal from said fluted stem and contacting the opposite end of said press fitted porous body; and (vi) an external portion integral in the stem adjacent to said suture ring member appointed to be attached to a foot or hand-shaped prosthesis.

The stem of the percutaneous implant device incorporates a biocompatible metal alloy and provides strength and biocompatibility properties as well as high tensile strength. The percutaneous implant device does not exert undue stresses when the fluted stem is inserted into a bone cavity of a limb. The inner cylindrical portion of the stem is press fitted to a porous outer body. Such inner cylindrical stem portion is preferably composed of sintered titanium fibers or titanium beads having at least 40-volume percent porosity. It can alternatively be composed of a metal foam having as much as 85 percent porosity. The porous outer body is press fitted against the cylindrical core portion of the stem with one end resting against the suture ring member. This arrangement prevents displacement of the porous outer body along the length of the stem, while the press fit prevents any rotation of the porous outer body. When the porous outer body is press fitted over the cylindrical core portion, the assembled stem behaves as a single unit. The end of the porous body that is distal from the suture ring member is provided with a female taper designed to engage with a male taper provided on the free end of the bone. Using this form of attachment, the male tapered fluted stem portion engages with the female taper drilled cavity within the bone. At the same time, the press fitted outer porous body female taper engages with the male taper, surgically created at the free end of the bone, thereby preventing any lateral displacement. This structure is a key factor that results in avoiding poor bonding of the implant with the bone, or poor bone in-growth. The bone is thus drilled using surgical tools provided so that the tapered fluted stem can be inserted and fitted into the bone. A male taper is created at the free end of the bone. The protruding portion of the porous outer body is used to secure the soft tissue. Such protruding portion is stitched using the suture ring holes therein, through which a needle carrying suture is inserted. In this manner, the female taper of the porous outer body contacts the bone while the outer surface of the porous outer body contacts the soft tissue.

Bone and tissue in-growth is thereby allowed within the porous body, providing biological attachment of the implant to the bone and soft tissue.

BRIEF DESCRIPTION OF DRAWINGS

The invention will be more fully understood and further advantages will become apparent when reference is had to the following detailed description and the accompanying drawings, in which:

FIG. 1b illustrates four schematic views of the percutaneous implant device, the first view 1.b.1 depicting the implant prior to assembly, FIGS. 1.b.2 and 1.b.3 depicting two views of the assembled percutaneous implant, and FIG. 1.b.4 illustrates the percutaneous implant device assembled and implanted within a bone;

FIG. 1c illustrates two schematic views of an extremity prosthetic foot for a canine adapted to be attached to the percutaneous implant device showing a side view in 1.c.1 and a bottom view in 1.c.2;

DESCRIPTION OF THE PREFERRED EMBODIMENTS

Figure 1A:
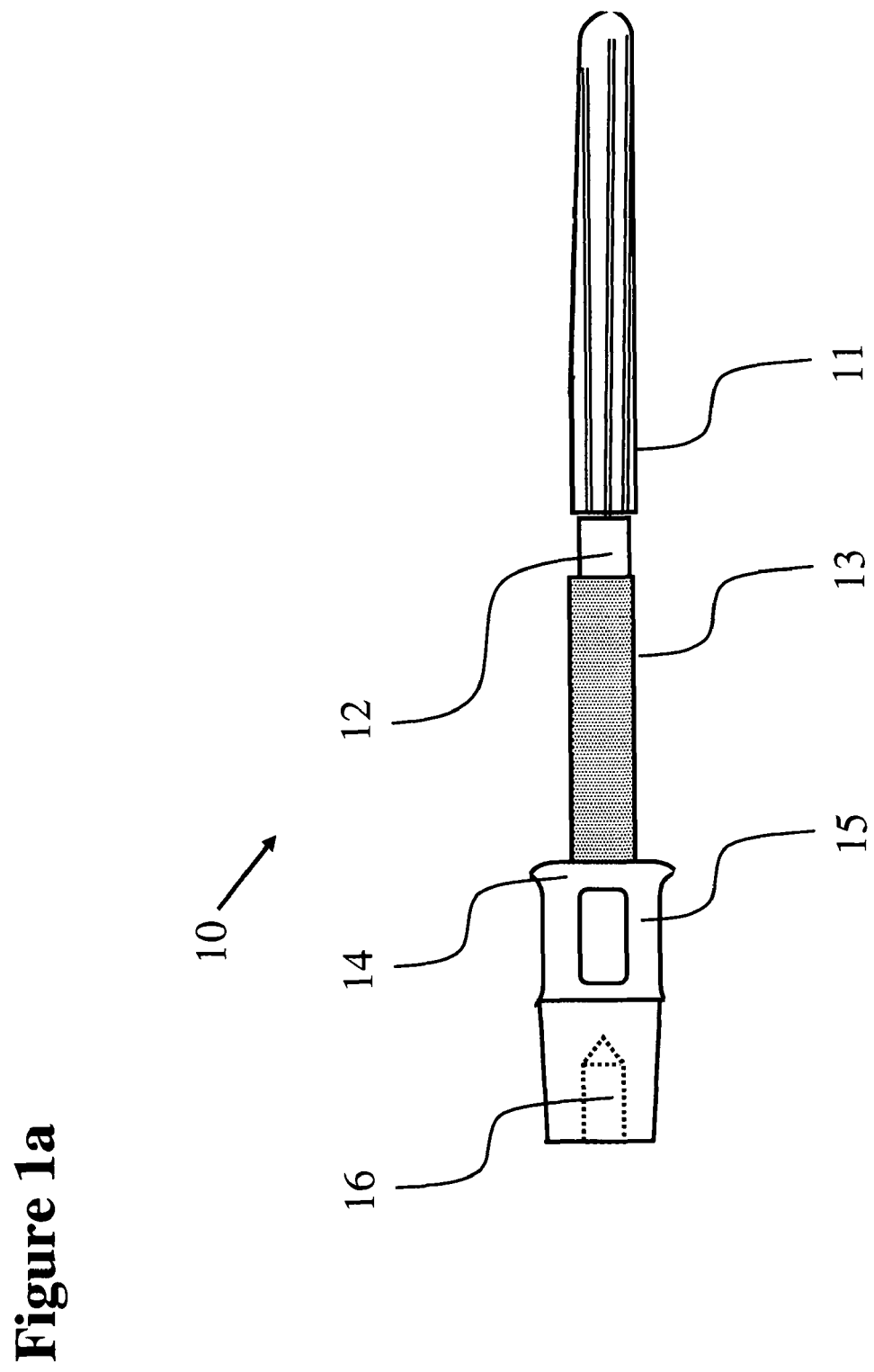
FIG. 1a is a schematic view of the percutaneous implant device.

Amputees, both in animals and humans, are generally assisted in returning to near normal activity through the attachment of an external prosthetic to the remnant stump of the limb. Coupling of the prosthesis is typically accomplished through coupling to the soft tissue of the remnant limb stump. However, this clinical approach to coupling presents many problems, including stump pain and sores, as well as physiological complications. Resulting sores create pain and consequent disuse of the limb. Physiological problems caused by failure of the prosthetic device to properly load the bone and soft tissues often result in atrophy of bone and muscle.

The percutaneous implant device is a novel implant design for replacing amputee limbs, which physiologically loads both bone and soft tissue. Preservation of bone and tissue is promoted, thereby mitigating or substantially eliminating pain associated with strapping a prosthetic to the stump. Advantageously, the percutaneous implant device provides a prosthesis, which allows for biologic attachment directly to the bone and soft tissues. The percutaneous implant device includes an external portion within the implant body for facilitating attachment of the device to an extremity, such as a foot or hand.

This invention relates to a percutaneous implant device for animal or human limb salvage. This implant device is attached to the bone segment located below the knee portion of the leg or in the ulnar portion of the arm. A female tapered cavity of a specified depth is drilled in the bone during a surgical procedure. The free end of the bone is surgically machined to provide a precise taper. The percutaneous implant device has a male tapered fluted portion that is designed to be inserted into the tapered cavity of the bone. The percutaneous implant device has a porous metal outer body that is press fitted over the cylindrical portion of the stem of the percutaneous implant device. A female taper mates with a male taper at the extremity of the bone, thereby securing the percutaneous implant device. The stem of the percutaneous implant device has an extension that carries the feet or hand shaped prosthesis.

The integral stem of the percutaneous implant device is made from titanium or cobalt-chromium alloy, which has high tensile strength and is completely biocompatible and corrosion resistant to body fluids. The stem has a male tapered fluted portion. An integral cylindrical inner core portion is adjacent to the tapered fluted portion. The cylindrical inner core is precisely dimensioned to provide press fit against a porous metal outer body made from sintered fiber, beads or foam. When the porous outer body is press fitted against the cylindrical inner core portion, the porous outer body becomes integral with the stem of the percutaneous implant device. The stem is provided with an integral suture ring adjacent to the cylindrical core region that is distal from the tapered fluted portion. During press fitting the porous outer body rests against the suture ring, which has a larger diameter than the porous outer body.

When the percutaneous implant device with the press fitted porous outer member is inserted into the tapered bone cavity, the tapered fluted portion of the stem engages the tapered bone cavity provided a tight fit of the percutaneous implant device. The male taper of the bone engages the female taper of the porous metal outer body that is press fitted over the cylindrical core portion of the percutaneous implant device, providing secure attachment and preventing any lateral movement. In growth of bone tissue or soft tissue into the porous titanium outer body requires minimal movement at this interface. Any movement results in poor tissue formation, preventing bone soft and bone tissue in-growth.

Since the force applied to the arm or leg has to be carried by the press fit, the quality of the press fit needs to be of sufficient interference to generate sufficient interface stresses, preventing movement of the components of the percutaneous implant device. Therefore, the cylindrical core portion of the stem is machined to a precise dimensional tolerance. Similarly, the bore of the porous metal outer body is machined to a precise dimensional tolerance. Typically, this press fit requires an interference of 0.005 mm to 0.20 mm (0.0002 inch to 0.008 inch), and preferably from about 0.01 mm to 0.015 mm (0.0004 inch to 0.0006 inch). That is, the cylindrical core is larger in diameter as compared to the bore of the porous metal outer body by this amount. When the porous metal body is press fitted with the cylindrical central core, the porous metal outer body rests against the suture ring portion of the percutaneous implant device. The female taper provided in the porous metal body points in the direction of the male tapered, fluted stem, ready to engage with the male taper surgically machined on the extremity of the bone. The specific level of interference would be predicated by the geometry and area of contact between the mating components. For example, the porous metal body inside bore could be provided with a plurality of ribs running longitudinally along the length thereof. Alternatively, the solid titanium core could have positive longitudinal splines capable of being press-fit into the porous metal body.

FIG. 1a illustrates generally at 10 a schematic view of the percutaneous implant device. FIG 1b illustrates views of the percutaneous implant device, and FIG. 1c illustrates views of an extremity (showing a prosthetic foot for a canine) appointed to be attached to the percutaneous implant device; FIG. 1.b.4 illustrates a view of the assembled implant within a bone. The numerical indicia used refer to equivalent parts of the implant. The percutaneous implant device includes an implant stem 5 having a male tapered fluted stem 11 appointed to be inserted within a bone canal. A cylindrical inner core 12 is integral with the tapered fluted stem 11, and a porous outer body member 13 is press fitted over the cylindrical inner core 12. The percutaneous implant device further includes integral suture ring member 14 on the stem for attaching soft tissue to the implant device 10. The porous titanium outer body member rests against the suture ring member 14 on one side and the other side has a female taper 13' appointed to attach to a surgically machined male taper 1' on the free extremity of a bone 1, as depicted in FIG. 1.b.4. An external portion 15 of the device 10 is appointed with attachment means 16 that is adapted to be attached to an extremity prosthesis, such as a foot or hand. The implant design of the percutaneous implant device is composed of two basic materials: (i) wherein the inner core 12 is made of titanium or cobalt-chrome to impart strength and biocompatibility; and (ii) wherein porous outer body member 13 is composed of a porous tantalum, titanium or niobium material capable of allowing bone and soft tissue to grow into it. These two (2) basic features or elements are utilized in order to achieve stable integration with the bone.

The interface with the bone is a tapered fit, via the tapered fluted stem 11, and between the female taper of the porous metal outer body member metal and the surgically machined male taper of the bone thereby providing better resistance to offset loads verses a flat surface to flat surface interface, which can have movements preventing bone in-growth. The soft tissues are attached to the outer surface of the porous metal outer body member 13 surrounding the suture ring member 14. This provides for a solid attachment of the soft tissue to the implant since the porous metal body is typically 37 mm (1.5 inches) long, and provides for significant attachment of soft tissue thereby promoting soft tissue in-growth. With these attachments, the external portion 15 of the implant device 10 can then be passed through the skin creating a percutaneous device capable of having a foot or hand attached thereto immediately after surgery. The method of integrating the implant device 10 with the bone and soft tissues, as is provided by the percutaneous implant device, provides the opportunity for these biologic materials to maintain their viability when loaded/stressed. Moreover, it is proposed that the method would provide better stress transfer and thereby be less painful to the patient.

Referring to FIG. 1b, FIG 1b.1 illustrates the implant stem 5 comprising the male tapered fluted stem 11 and cylindrical inner core 12, prior to assembly with the porous metal outer body member 13 . FIGS. 1.b.2 and 1.b.3 illustrate two photographic views of the assembled percutaneous implant, while FIG. 1.b.4 illustrates the assembled device implanted in a bone. Referring to FIGS 1b.1-1b.4 the percutaneous implant device comprises an implant stem 5 having integral portions (male tapered fluted stem 11, cylindrical inner core 12, suture ring member 14, and external portion 15) and a porous metal outer body member 13 that is press fitted onto the implant stem 5. The implant stem 5 is composed of a biologically compatible metal alloy and the porous metal outer body member 13 includes an outer surface and is composed of a material adapted for bone and soft tissue in growth characteristics. Specifically, porous metal outer body member 13 is composed of a porous tantalum, titanium or niobium material, as indicated by the shading, capable of allowing bone and soft tissue to grow into it. The implant stem 5 includes a male tapered fluted stem portion 11 adapted to be inserted into a female tapered cavity drilled within a bone of a broken limb. The implant stem 5 includes a cylindrical inner portion/core 12 abutting the male tapered fluted stem 11. The cylindrical inner portion/core 12 has a cylindrical core diameter 12' adapted for press fitting of the porous metal outer body member 13 thereon. The porous metal outer body member 13 includes a central aperture 13a with a bore diameter 13a' that is smaller than the cylindrical core diameter 12' by an interference amount for precise dimensional tolerance to integrally mate the porous metal outer body member 13 with the cylindrical inner portion 12 of the implant stem 5. The implant stem 5 further includes suture ring 14 abutting the cylindrical inner portion 12 and located distal from the male tapered fluted stem 11. One end of the porous metal outer body member 13 abuts the suture ring 14 with suture holes 14'. Another end of the porous metal outer body member 13 has a female taper 13' abutting the male tapered fluted stem 11 and being adapted to mate with a male taper surgically created on a bone end (See FIG. 5). The implant stem's 5 external member/portion 15 extends from the suture ring 14 and is adapted for attachment to a hand or foot prosthesis (FIG. 1c).

Referring to FIG. 1.c, the FIG. 1.c.1 shows a side view of the foot prosthesis, showing the taper provided at 17 to mate with the taper of the external portion 15 of the stem. FIG. 1.c.2 shows the bottom of the foot prosthesis showing the radiused contact pad at 18

Figure 2:
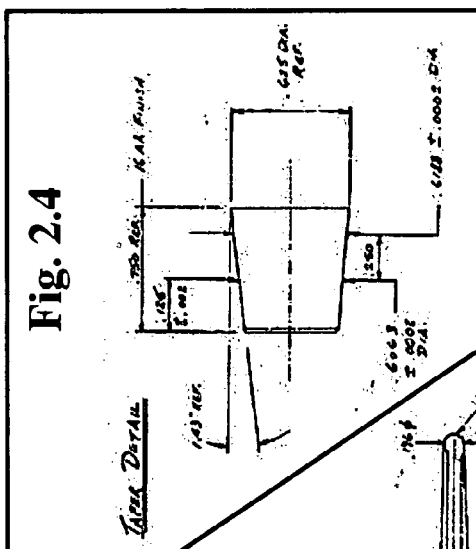
FIG. 2 illustrates design features of the implant stem and cylindrical central core with the entire part shown in FIG. 2.1, the details of the suture ring in FIG. 2.2, the end taper for attachment to prosthetic extension in FIG. 2.4 and details of fluted taper end in FIG. 2.3.
Figure 2:
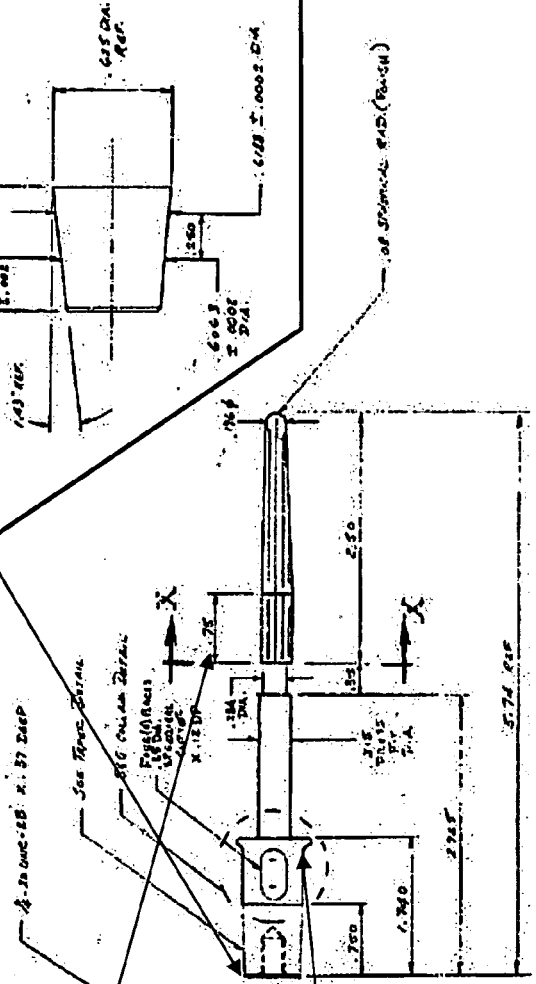
Figure 2:
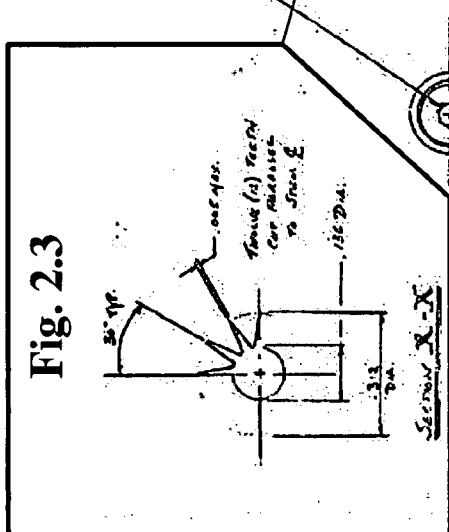
Figure 2:
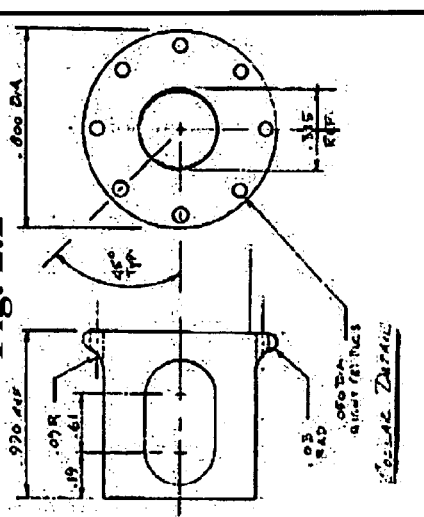
Figure 3:
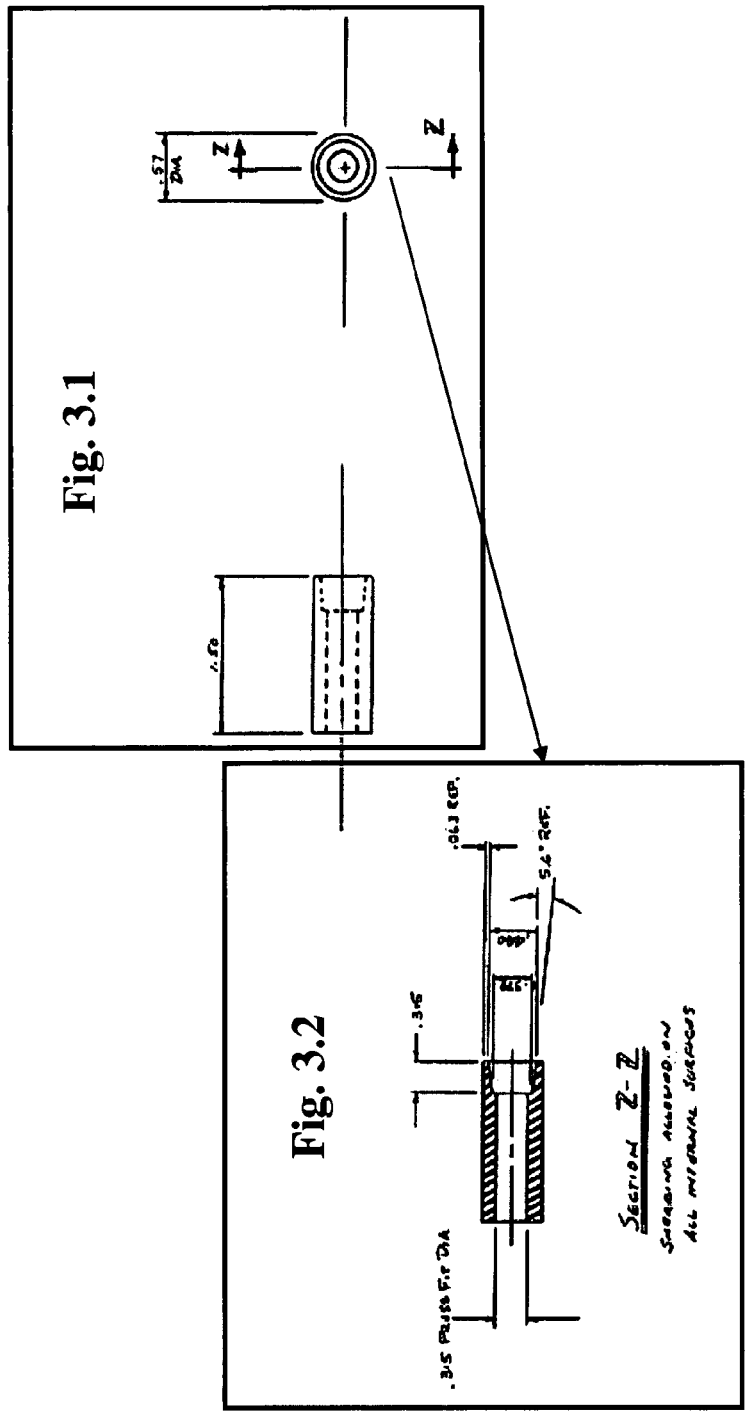
FIG. 3 illustrates design features of the porous titanium outer body showing its dimensions in FIG. 3.1 and its cross sectional detail I FIG. 3.2.

FIGS. 2 through 3 illustrate the design elements and dimensional features of the percutaneous implant device and method of use. In both figures, dimensions shown are in inches. FIG. 2 illustrates the design and dimensional details of the implant stem in FIG. 2.1. The FIG. 2.2 shows the details of the suture ring attached to the cylindrical central core, FIG. 2.4 shows the detail of the taper of the external connection end of the percutaneous implant designed to fit into a foot or hand prosthesis and FIG. 2.3 illustrates the constructional details at the section x-x of the tapered fluted end of the percutaneous implant that enters the bone canal. FIG. 3 illustrates the design and dimensional details of the porous metal outer body member. FIG. 3.1 illustrates the overall dimension of the porous metal outer body member, while FIG. 3.2 illustrates the cross section along the section z-z. Note that the cylindrical inner core of the stem of FIG. 2 is provided with dimensional tolerance to provide a press fit against the central aperture of the porous metal outer body of FIG. 3. When the porous metal outer body is press fitted over the cylindrical inner core while resting against the suture ring member, it extends. The extension covers the 7.5 to 15 mm (0.3-0.5 inch) recess section and the cylindrical fluted section of the stem.

Figure 4:
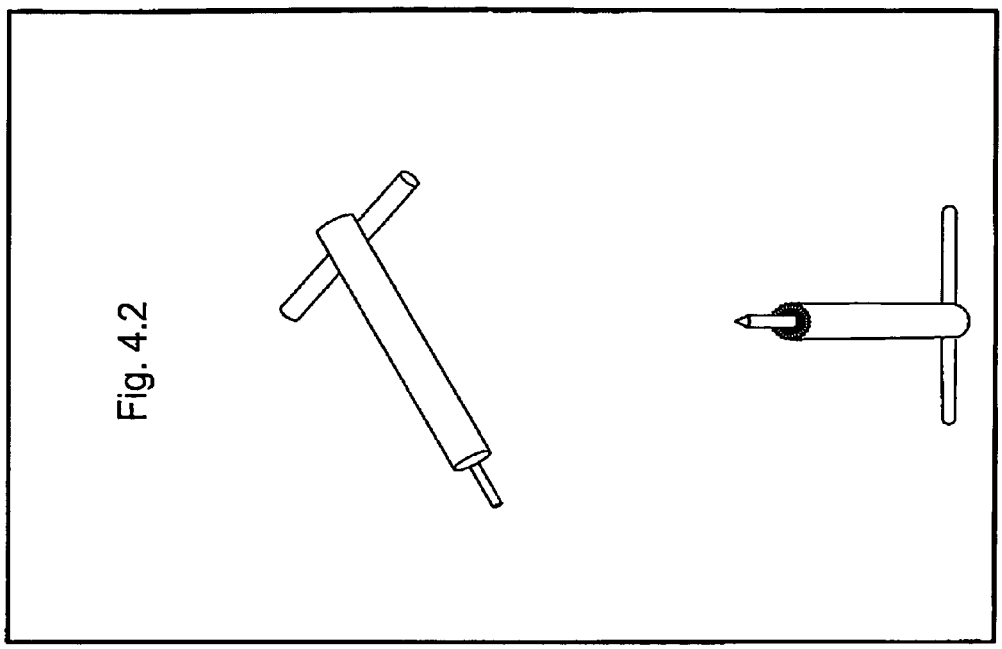
FIG. 4 illustrates an example case of a pre-operative radiograph in FIG. 4.1 and drilled 5 mm diameter bone canal for a depth of 60 mm followed by planar cutting bone extremity using distal bone planer shown in two views of FIG. 4.2.
Figure 4:
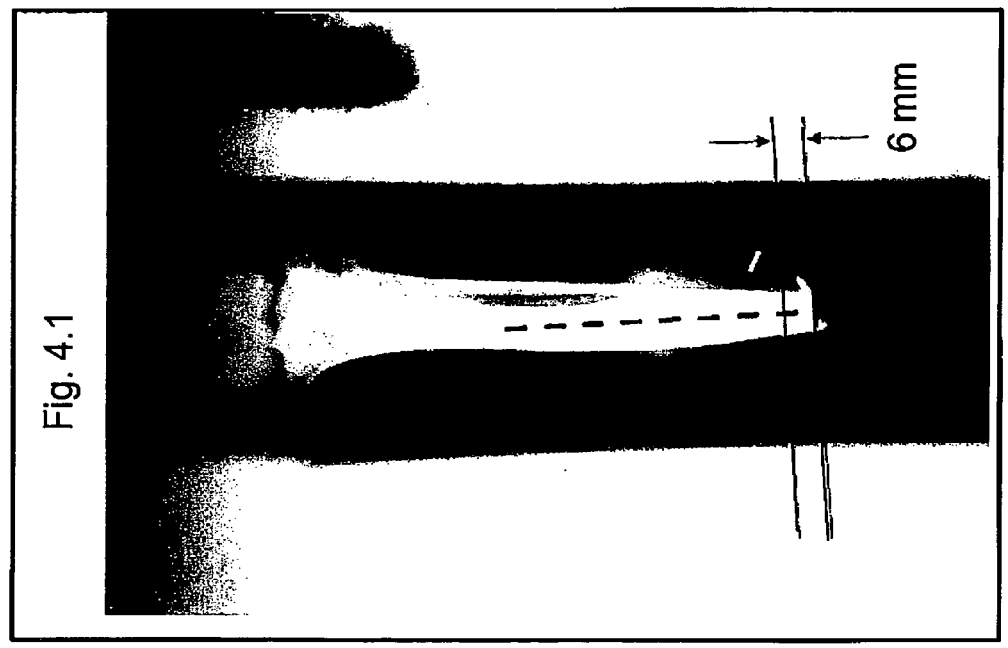
Figure 5:
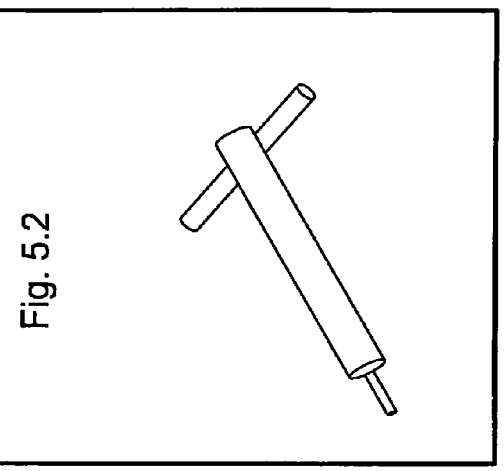
FIG. 5 illustrates in FIG. 5.1 a radiograph of the second part of the surgical procedure wherein the free end of the bone which has been made perpendicular to the bone is now provided with a conical male taper using conical bone planer shown in FIG. 5.2 to a chamfer depth of 8 mm.
Figure 5:
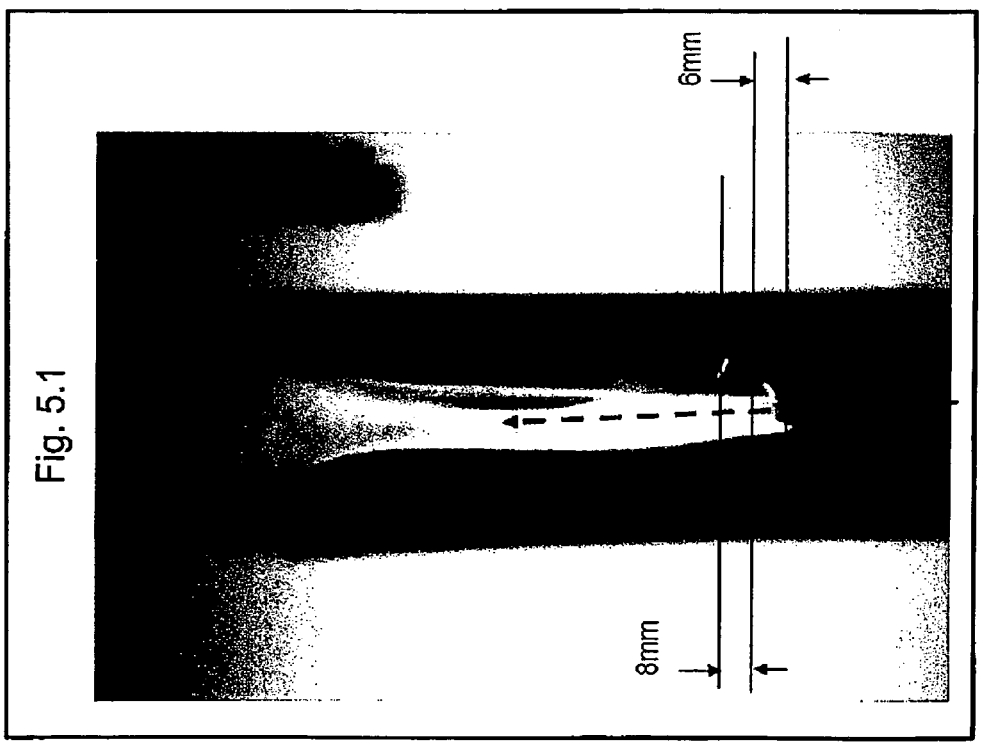
Figure 6:
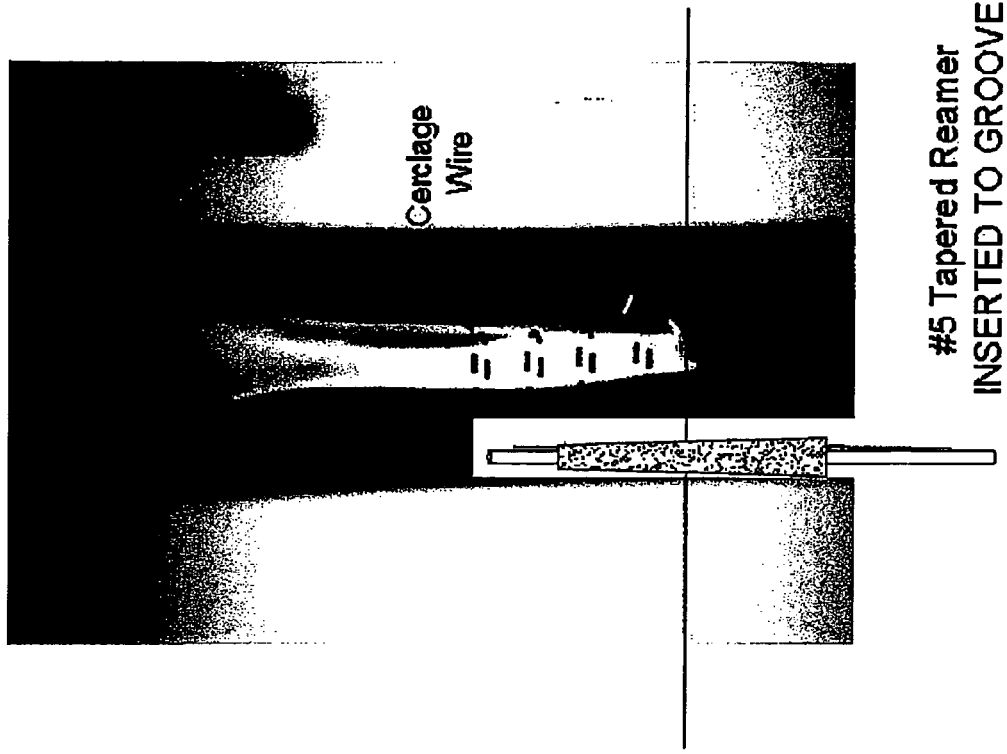
FIG. 6 illustrates the third surgical step involved with preparation of the bone cavity, wherein four cerclage wires are inserted and the 5 mm bone canal is taper reamed.
Figure 7:
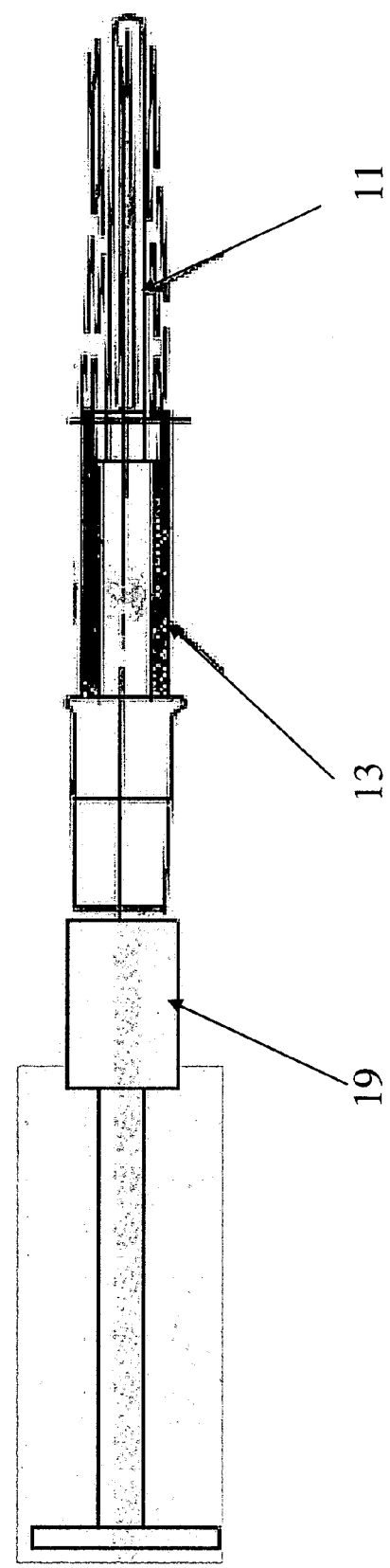
FIG. 7 illustrates the fourth step of the surgical procedure, wherein the assembled percutaneous implant is first inserted into the bone canal with hand pressure, and pressed in by an impactor.
Figure 8:
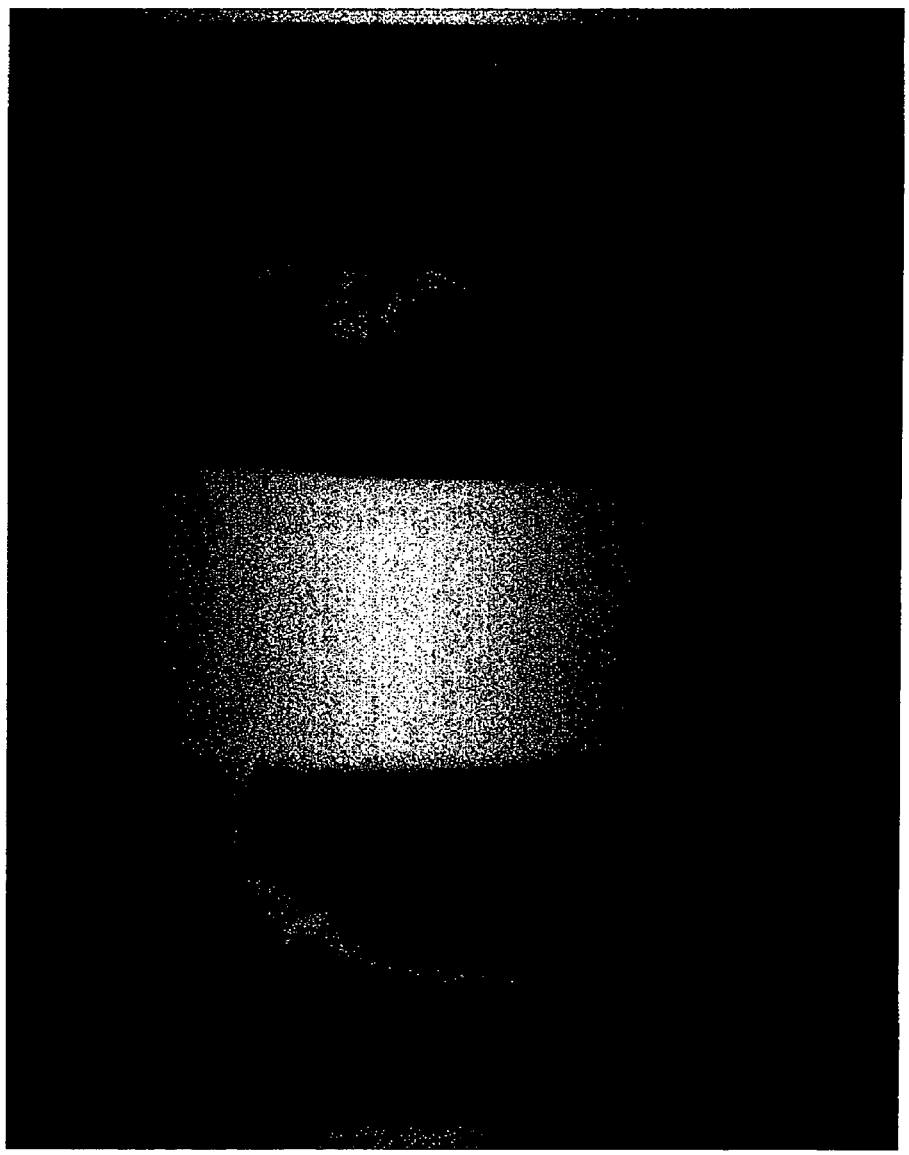
FIG. 8 illustrates two views of an example case of a pre-operative radiograph showing side by side the amputated canine limbs.
Figure 9:
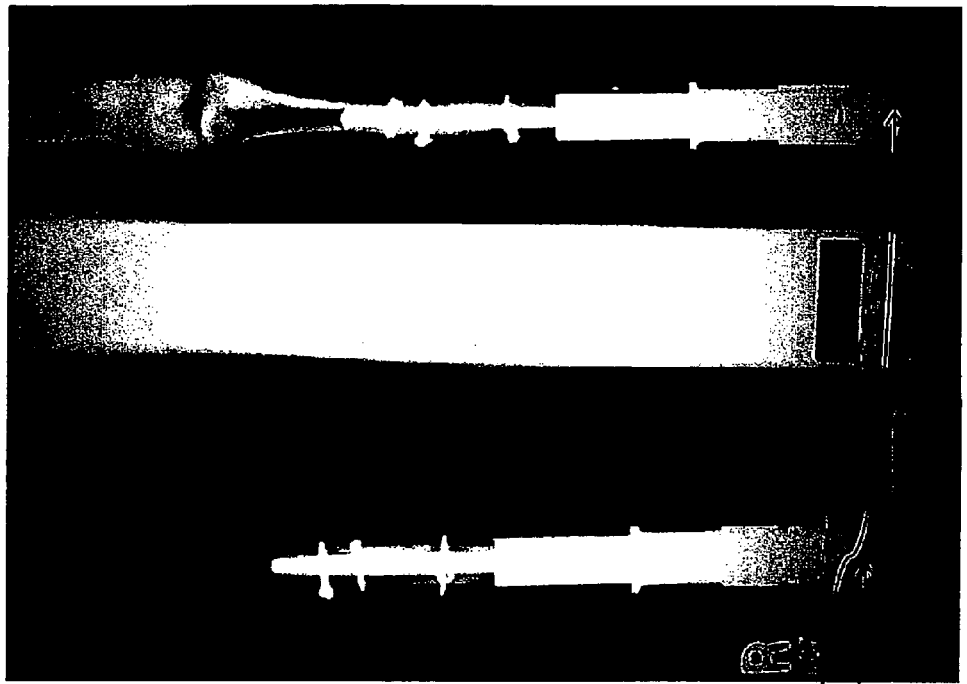
FIG. 9 illustrates collectively a post-operative photograph and a radiograph showing the amputated canine limbs with a foot prosthesis attachment in FIG. 9.1 and a photograph of the foot prosthesis is shown in FIG. 9.2 and FIG. 9.3 shows photograph of an actual canine patient in the operating room during attachment of foot prosthesis immediately following percutaneous implant procedure.
Figure 9:
Figure 9:
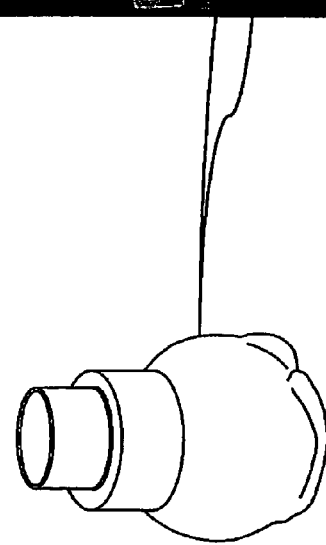

FIGS. 4 through 7 illustrate the surgical technique and method of use of the percutaneous implant device. FIG. 4 illustrates in FIG. 4.1 an example case involving a pre-operative radiograph. The bone is first provided with a bone cavity of 5 mm to a drill depth of approximately 60 mm using a surgical drill. The free end of the bone is planed using a distal planer shown in the two views of FIG. 4.2 to assure that the end of the bone is perpendicular to the bone canal centerline. The pilot on the bone planer instrument is also 5 mm and therefore freely enters the drilled bone canal. FIG. 5 shows the second part of the surgical procedure wherein the free end of the bone, which has been made perpendicular to the bone is now provided with a conical male taper or a chamfer using a conical bone planer to a depth of 8 mm. The radiograph illustrates the bone at this condition. FIG. 5.1 shows a radiograph showing the depth to which the end of the bone will be provided with a conical taper. FIG. 5.2 shows a photograph of the conical bone planer. FIG. 6 illustrates the third surgical step of the preparation of the bone cavity. From the first 10 mm of the free end of the bone cavity, the tibial cortex is cerclaged to place cerclage wires approximately 15 mm apart totaling 4 cerclage wires. Tapered reamers of size #2 and #3 are inserted into the bone canal and a tapered bone cavity is now created. FIG. 6 also shows a radiograph of the bone in this third step of the surgical procedure. FIG. 7 shows the fourth step of the surgical procedure. The assembled percutaneous implant with stem 12 and porous metal outer body member 13 is inserted into the bone canal with hand pressure. The fluted tapered portion has a dimension ranging from 0.312 inches (7.9 mm) to an end, which has a diameter of 0.196 inches (4.97 mm) as shown in FIG. 2. Therefore, the drilled 5 mm bone canal will accept the fluted end of the stem. The implant will be outside the bone canal at this stage by approximately 15 mm depending on the strength of the bone. An impactor 19 is positioned at the end of the percutaneous implant. If the implant does not proceed easily into the one canal, it can be removed at this stage and the bone canal is then enlarged, using a #5 tapered reamer. This procedure should reduce the level of interference between the percutaneous implant and the bone cavity. The larger flutes of the tapered fluted stem will cut into the bone securing the percutaneous implant. Once the percuaneous implant is fully seated inside the bone canal, soft skin tissue may be attached surrounding the porous metal outer body. The skin may then be attached to the suture ring. FIG. 8 illustrates an example case: involving a pre-operative radiograph of amputee limbs of a canine in need of prosthesis with two radiographic views perpendicular to each other. FIG. 9 illustrates in FIG. 9.1 an example case involving a post-operative radiograph with views perpendicular to each other showing the percutaneous implant and the attached prosthesis. FIG. 9.2 shows a photograph of the foot prosthesis. Each of the limbs is fitted with a percutaneous implant device and foot prosthesis. FIG. 9.2 shows a canine patient being fitted with foot prosthesis into the percutaneous implant immediately during surgical procedure.

While the subject invention uses stems made from titanium alloy or cobalt chromium alloy, other bio-compatible materials such as tantalum, niobium may be used to fabricate the stem.

The percutaneous implant device comprises, in combination, the following salient features:

1. an integral biocompatible metal alloy stem and a press fitted porous metal outer body;
2. the integral stem having a fluted male tapered stem member designed to be inserted into a female tapered cavity drilled within the bone of a broken limb;
3. the integral stem having a cylindrical portion contacting the fluted male tapered stem portion, the cylindrical portion having precise dimensional tolerance to accept press fitting of the porous metal outer body;
4. the porous metal outer body having a central aperture with precise dimensional tolerance to mate with the cylindrical inner portion of the stem;
5. the integral stem having a suture ring contacting the distal side from the fluted male tapered stem;
6. one end of the press fitted porous metal outer body contacting the suture ring;
7. the other end of the porous metal outer body having a female taper on the side distal from the stem suture ring contacting side to mate with a corresponding male taper surgically created on the bone end;
8. the integral stem having an external member extending from said suture ring member for attachment to a hand or foot prosthesis;

whereby the porous metal outer body upon press fitting over the stem cylindrical portion functions as a single unit and is inserted into a surgically machined bone segment of a broken bone, the fluted male taper of the stem is inserted into a female taped bone cavity and the male outer taper at the bone extremity contacts the female taper of the porous metal outer body, providing secure attachment of the bone and promoting bone in-growth, while the soft tissue contacts the extending portion of the porous metal outer body, promoting soft tissue in-growth into the implant.

Salient features of a surgical procedure for using the percutaneous implant device are set forth below:

1. sectioning a broken limb perpendicular to the length of the bone with some soft tissue extending beyond the sectioned bone;
2. drilling a bone canal within the bone to a depth matching the specifications of the percutaneous implant device forming a bone canal;
3. machining the free end of the bone using a conical planer, to form a precise male taper equivalent to the specification of the female taper of the porous biocompatible metal outer body of the percutaneous implant device stem;
4. enlarging the bone canal with a surgical tapered reamer;
5. inserting the fluted male tapered stem of the percutaneous implant device with the porous metal outer body already press fitted on the cylindrical inner core into the tapered bone cavity using hand pressure followed by an impactor until the male taper at the free end of the bone contacts seats against the female taper of the porous metal outer body;
6. extending the soft tissue to contact the external surface of the porous metal outer body, enclosing the suture ring; and
7. inserting a suture needle carrying a suture through the holes provided in the suture ring to attach the soft tissue and skin to the porous metal outer body and the suture ring, whereby the percutaneous implant device with press fitted porous metal outer body is secured immediately after surgery by contact between the fluted tapered stem portion and the bone tissue on top, so that the bone seated at the bottom against the female taper of the porous metal outer body prevents lateral displacement and promotes bone in-growth, and the soft tissue contacts the porous metal outer body, and is secured by skin sutures surrounding a suture ring, thereby providing in-growth soft tissue.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. A percutaneous implant device, comprising:
   a. a biologically compatible metal alloy implant stem and a porous metal outer body member adapted for bone and soft tissue in-growth;
   b. said implant stem having a male tapered fluted stem portion adapted to be inserted into a female tapered cavity drilled within a bone of a broken limb;
   c. said implant stem having a cylindrical inner portion extending from and abutting said male tapered fluted stem portion, the cylindrical inner portion having a cylindrical core diameter adapted for press fitting said porous metal outer body member thereon;
   d. said porous metal outer body member having a central aperture with a bore diameter that is smaller than said cylindrical core diameter by an interference amount to integrally mate said porous metal outer body member with said cylindrical inner portion of the implant stem;
   e. said implant stem having a suture ring abutting said cylindrical inner portion and located distal from said male tapered fluted stem portion;
   f. one end of said porous metal outer body member abutting said suture ring;
   g. another end of said porous metal outer body member distal from said suture ring having a female taper abutting said male tapered fluted stem portion and being adapted to fit around and mate with a male taper surgically created on a bone end;
   h. said implant stem having an external member integral to said implant stem extending from said suture ring adapted for attachment to a hand of foot prosthesis;
   whereby the porous metal outer body is adapted to be press fit over the cylindrical inner portion so that said percutaneous implant device functions as a single unit;
   whereby the male tapered fluted stem portion and the female taper of the porous metal outer body are adapted for bone contact, generating bone in-growth;
   whereby said suture ring is adapted for suturing soft tissue thereto;
   whereby said outer surface of said porous metal body member is adapted to contact soft tissue generating soft tissue in-growth and thereby preventing lateral and longitudinal displacement of said percutaneous implant during healing and promoting bone and soft tissue in-growth.

2. A percutaneous implant device as recited by claim 1, wherein said interference amount for press fitting of said cylindrical inner portion of said implant stem and central aperture of said porous metal body is 0.005 to 0.20 mm.

3. A percutaneous implant device as recited by claim 1, wherein said porous metal outer body comprises sintered beads, sintered wire segments or foam.

4. A percutaneous implant device as recited by claim 1, wherein said male tapered fluted stem portion is adapted to connect to said female tapered bone cavity with interference.

5. A percutaneous implant device as recited by claim 1, wherein said female taper of said porous metal outer body member has a length of about 8 mm (0.351 inches).

6. A percutaneous implant device as recited by claim 1, wherein said porous metal outer body member has a length of 37 mm, and is adapted to provide soft tissue contact for soft tissue in-growth.

7. A percutaneous implant device as recited by claim 1, wherein said suture ring has suture holes adapted for suturing skin surrounding an outer surface of said suture ring.

8. A percutaneous implant device, comprising:
   a. a biologically compatible titanium or cobalt-chromium alloy implant stem and a porous tantalum outer body member adapted for bone and soft tissue in-growth;
   b. said implant stem having a male tapered fluted stem portion adapted to be inserted into a female tapered cavity drilled within the bone of a broken limb;
   c. said implant stem having a cylindrical inner portion extending from and abutting said male tapered fluted stem portion, the cylindrical inner portion having a cylindrical core diameter adapted for press fitting said porous tantalum outer body member thereon;
   d. said porous tantalum outer body member having a central aperture with a bore diameter that is smaller than said cylindrical core diameter by an interference amount to integrally mate said porous metal outer body member with said cylindrical inner portion of the implant stem;
   e. said implant stem having a suture ring abutting said cylindrical inner portion and located distal from said male tapered fluted stem portion;
   f. one end of said porous tantalum outer body member abutting said suture ring;
   g. another end of said porous metal outer body member distal from said suture ring having a female taper abutting said male tapered fluted stem portion and being adapted to fit around and mate with a male taper surgically created on a bone end
   h. said implant stem having an external member integral to said implant stem extending from said suture ring adapted for attachment to a hand or foot prosthesis;
   whereby the porous tantalum outer body is press fitted over the cylindrical inner portion so that said percutaneous implant device functions as a single unit;
   whereby said fluted male tapered stem and said female taper of said porous tantalum outer body member are appointed for bone contact for generating bone in-growth;
   whereby said suture ring is appointed to be sutured to soft tissue and said porous tantalum body member is appointed to contact soft tissue for generating soft tissue in-growth thereby preventing lateral and longitudinal displacement of said percutaneous implant during healing and promoting bone and soft tissue in-growth.

9. A percutaneous implant device as recited by claim 8, wherein said interference amount for press fitting of said cylindrical inner portion of said implant stem and central aperture of said porous tantalum outer body member is 0.01 to 0.015 mm.

10. A percutaneous implant device as recited by claim 8, wherein said male tapered fluted stem portion is adapted to connect to said female tapered bone cavity with interference.

* * * * *